(12) United States Patent
Yamakoshi

(10) Patent No.: US 8,275,433 B2
(45) Date of Patent: Sep. 25, 2012

(54) NON-INVASIVE BLOOD CONSTITUENT MEASURING INSTRUMENT AND MEASURING METHOD

(75) Inventor: Ken-ichi Yamakoshi, Kanazawa (JP)

(73) Assignee: yu.sys.corporation, Ishikawa-ken (JP)

( * ) Notice: Subject to any disclaimer, the term of this patent is extended or adjusted under 35 U.S.C. 154(b) by 1329 days.

(21) Appl. No.: 11/819,324

(22) Filed: Jun. 26, 2007

(65) Prior Publication Data

US 2008/0027297 A1 Jan. 31, 2008

Related U.S. Application Data

(63) Continuation-in-part of application No. 10/508,833, filed as application No. PCT/JP03/03587 on Mar. 25, 2003, now abandoned.

(30) Foreign Application Priority Data

Mar. 25, 2002 (JP) .................................. 2002-083587

(51) Int. Cl.
*A61B 5/1455* (2006.01)
(52) U.S. Cl. ........................................ 600/316; 600/310
(58) Field of Classification Search ............ 600/309–344
See application file for complete search history.

(56) References Cited

U.S. PATENT DOCUMENTS

| | | | |
|---|---|---|---|
| 4,975,581 A | 12/1990 | Robinson et al. | |
| 5,068,536 A * | 11/1991 | Rosenthal ................ | 250/341.5 |
| 5,348,003 A | 9/1994 | Caro | |
| 5,355,880 A | 10/1994 | Thomas et al. | |
| 5,372,135 A | 12/1994 | Mendelson et al. | |
| 5,522,388 A | 6/1996 | Ishikawa et al. | |
| 5,571,723 A | 11/1996 | Evans et al. | |
| 5,630,413 A | 5/1997 | Thomas et al. | |
| 6,172,743 B1 | 1/2001 | Kley et al. | |
| 6,181,957 B1 | 1/2001 | Lambert et al. | |
| 6,280,381 B1 | 8/2001 | Malin et al. | |
| 6,289,230 B1 | 9/2001 | Chaiken et al. | |
| 6,868,285 B2 | 3/2005 | Muller-Dethlefs | |

FOREIGN PATENT DOCUMENTS

| | | |
|---|---|---|
| CN | 1214769 A | 4/1999 |
| EP | 0404 562 | 12/1990 |
| EP | 586025 | 3/1994 |

(Continued)

OTHER PUBLICATIONS

International Search Report, PCT/JP03/03587, dated May 13, 2003.

(Continued)

*Primary Examiner* — Eric Winakur
*Assistant Examiner* — Marjan Fardanesh
(74) *Attorney, Agent, or Firm* — Banner & Witcoff, Ltd.

(57) ABSTRACT

A non-invasive blood constituents measuring instrument measures blood constituent values including blood glucose concentration in a living body non-invasively. The instrument is composed of a light source 11 to irradiate a light containing plural wavelengths to a living body 13, a light receiver 14 to detect the light transmitted through a living body or reflected and scattered thereon, a spectrum analyzer 15 to analyze the light transmitted through the living body or reflected thereon at different times, a subtraction processor 18 to generate spectrum subtraction from the spectrum of the light at the different times measured by the spectrum analyzer 15, and a blood glucose concentration predictor 21 into which the output data of the subtraction processor 18 are input and which outputs a blood constituent value.

14 Claims, 10 Drawing Sheets

FOREIGN PATENT DOCUMENTS

| | | |
|---|---|---|
| JP | 3-114441 | 5/1991 |
| JP | 6-178767 | 6/1994 |
| JP | 07-088105 | 4/1995 |
| JP | 2000-23947 | 1/2000 |
| JP | 200-60826 | 2/2000 |
| JP | 2000-060826 | 2/2000 |
| WO | WO 97/28438 | 8/1997 |
| WO | WO 0191632 | 12/2001 |

OTHER PUBLICATIONS

Supplementary European Search Report, EP 03 71 2898 (PCT/JP0303687) dated Mar. 30, 2007.

Japanese Application 2003-577737, Office Action dated Sep. 9, 2008.

* cited by examiner

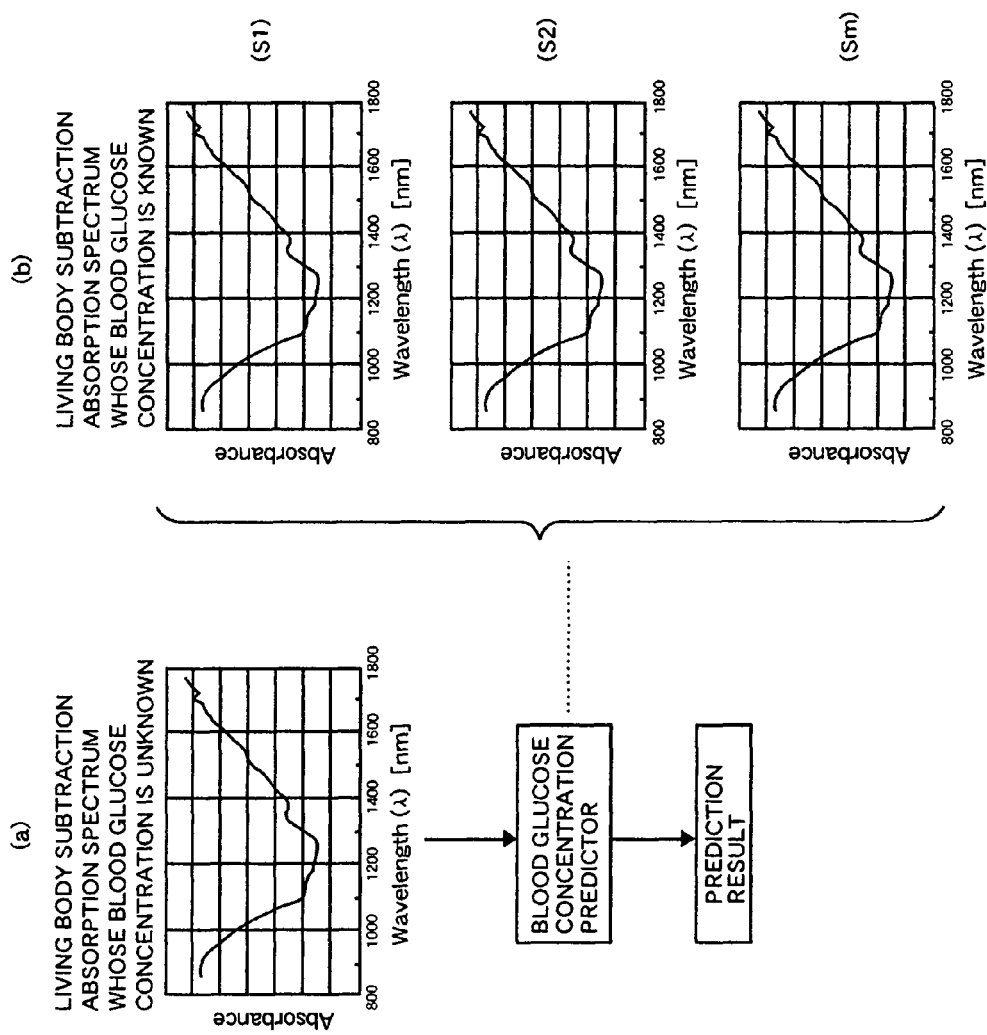

NON-INVASIVE BLOOD CONSTITUENT MEASURING INSTRUMENT AND MEASURING METHOD

This application is a continuation in part of U.S. patent application Ser. No. 10/508,833 filed on Apr. 14, 2005, now abandoned entitled "NON-INVASIVE BLOOD CONSTITUENT MEASURING INSTRUMENT AND MEASURING METHOD", which is a National Stage application of co-pending PCT application PCT/JP03/03587 filed on Mar. 25, 2003, which claims the benefit of priority to Japanese Patent Application No. 2002-083587, filed on Mar. 25, 2002. The contents of the noted applications are herein incorporated by reference in their entireties.

FIELD OF THE INVENTION

The present invention relates to an instrument and a method for measuring blood biochemical constituent including blood glucose concentration and, more particularly, to a non-invasive blood constituent measuring instrument and a method for measuring blood glucose concentration without sampling blood from a living body.

Diabetes that are collecting public attentions as a representative of lifestyle-related diseases are increasing recent years for aging and change in life-style. It is so far a general practice to measure blood glucose concentration by sampling a small amount of blood. However, it is strongly desired to reduce pain and botheration associated with the blood sampling. In addition, there is no other method available than the blood examination for measuring blood biochemical constituent.

On the other hand, a non-invasive measurement using near infrared light is collecting attentions for extremely low risk to living bodies and the possibility for measurement of items so far impossible by existing measuring methods. For example, glucose has an inherent absorption band derived from its constituents in this wavelength band and various methods are reported (Reference Literature: Ozaki Yukihiro, Practical Spectroscopy Series No. 4 "Medical Application of Spectroscopy", IPC)

For example, according to the reference literature, a method to obtain blood glucose concentration by irradiating an infrared light to a fingertip and through the computation of its transmitted light by a computer is proposed. For this method, however, it is very difficult to estimate glucose concentration in blood from the transmitted light obtained and thus a method to estimate glucose concentration using a multi-regression analysis is also proposed.

However, the absorption band inherent to glucose in the near infrared range overlaps on other constituent absorption ranges of protein materials, etc. and it is difficult to separate an absorption characteristic coming from glucose only and absorption characteristic of other material and therefore, there is a question in measuring accuracy and reproducibility of measurement and the proposed method is not yet put in practical use.

Further, a glucose measuring method using the above-mentioned multi-regression analysis is reported in the above-mentioned reference literature as shown below. That is, this method is to measure glucose in blood serum using the PLS method (partial least squares analysis) that is one of chemometrics by measuring infrared spectrum with lights in two wavelength ranges of 1325-1800 nm and 2035-2375 nm applied to glucose sample melted in blood serum.

However, as reported that a near infrared spectroscope made by NIR System Corp. according to the transmission penetration method using a quartz photocell in 0.5 mm light path length in the measurement, a quartz photocell was used in the measurement and is not a non-invasive measurement by irradiating light to living bodies.

In a non-invasive blood glucose concentration measuring method using a conventional absorption analysis method, the glucose absorption band overlaps the absorption ranges of other biological tissues in living bodies such as bones, blue pipes, muscles and it is difficult to separate the ranges and the accurate measurement is not feasible and is therefore not put in practical use.

Accordingly, it is an object of the present invention to provide a non-invasive blood glucose measuring instrument and a measuring method capable of solving the above-mentioned problems and measuring blood glucose concentration simply and highly accurately.

SUMMARY OF THE INVENTION

A non-invasive blood constituent measuring instrument according to an embodiment of the present invention includes a light source for irradiating light including plural wavelengths to a living body whose blood constituents are unknown; a light receiver to detect light transmitted through the living body or reflecting thereon; a spectrum analyzer to which the output signal of the light receiver is supplied and which analyzes spectrum of the light transmitted through the living body or reflected therefrom at different times having a shorter time intervals than the time cycle of the arterial waveform cycle; a spectrum subtraction generator to generate spectrum subtraction from the spectrum of the light measured by the spectrum analyzer at the different times having a shorter time intervals than the time cycle of the arterial waveform cycle; and a blood constituents predictor into which the output data of the spectrum subtraction generator is input and which outputs the blood constituents; wherein the blood constituents predictor compares the spectrum subtraction of the unknown constituents blood with a plurality of sample spectrum subtractions which are obtained from a living body whose blood constituents are known in a similar manner as obtained from a living body whose blood constituents are unknown and predicts the blood constituents of the unknown constituents blood.

Further, in the non-invasive blood constituent measuring instrument, a blood constituents predictor is provided with a multi-regression analyzing model using the plurality of the sample spectrum subtractions as an explanatory variable and blood constituent values as an objective variable, wherein the spectrum subtraction data obtained from bloods having known blood constituents are input into the multi-regression analyzing model as an explanatory variable, the objective variable is computed from the multi-regression analyzing model and output as a blood constituent value.

Further, the non-invasive blood glucose concentration measuring instrument according to the embodiment of the present invention is composed of a light source to irradiate a light containing plural wavelengths to a living body whose blood glucose concentration is unknown; a light receiver to detect the light transmitted through a living body or reflected therefrom; a spectrum analyzer to which the output signal of the light receiver is supplied and which analyzes spectrum of the light transmitted through the living body or reflected therefrom at different times having a shorter time intervals than the time cycle of the arterial waveform cycle; a spectrum subtraction generator to generate spectrum subtraction from the spectrum of the light measured by the spectrum analyzer at the different times having a shorter time intervals than the time cycle of the arterial waveform cycle; and a blood glucose concentration predictor into which the output data of the spectrum subtraction generator is input and which outputs the blood glucose concentration; wherein the blood glucose concentration predictor compares the spectrum subtraction of the unknown glucose concentration with a plurality of sample spectrum subtractions which are obtained from a living body whose blood glucose concentration is known in a similar manner as obtained from the living body whose blood glucose concentration is unknown described and predicts the blood glucose concentration of the unknown constituents blood.

Further, in the blood glucose concentration predictor according to the embodiment of the present invention, the blood glucose concentration predictor is constructed with a multi-regression analyzing model into which spectrum subtraction data of plural whole blood samples of known blood constituent is input as the explanatory variable and in which the blood glucose concentration is computed as an objective variable and output as blood glucose concentration.

A non-invasive blood constituent measuring method according to an embodiment of the present invention includes the steps of irradiating a light containing plural wavelengths to a living body whose blood constituents are unknown; detecting light transmitted through or reflected from the living body and converting it into an electric signal; analyzing spectrum of the light transmitted through the living body or reflected therefrom at different times using the converted electric signal; generating spectrum subtraction from the spectrum of the light at the different times; and predicting corresponding blood constituents from the spectrum subtraction; wherein the spectrum subtraction of the unknown constituents blood is compared with a plurality of sample spectrum subtractions which are obtained from a living body whose blood constituents are known in a similar manner as obtained from the living body whose blood constituents are unknown and thereby the blood constituents of the unknown constituents blood is predicted.

Further, in the blood constituent predicting steps according to the embodiment of the present invention, the blood constituent predicting step further includes steps of preparing a multi-regression analyzing model, into which spectrum data of plural whole blood samples having known blood constituent is input as an explanatory variable and blood constituent is output as an objective variable, inputting the spectrum subtraction data obtained from blood of which blood constituent is not known as an explanatory variable, and outputting the blood constituent as an objective variable.

Further, a non-invasive measuring method of blood glucose concentration according to an embodiment of the present invention includes the steps of: irradiating a light containing plural wavelengths to a living body whose blood glucose concentration is unknown; detecting light transmitted through or reflected from the living body and converting it into an electric signal; analyzing spectrum of the light transmitted through the living body or reflected therefrom at different times using the converted electric signal; generating spectrum subtraction from the spectrum of the light at the different times; and predicting corresponding blood glucose concentration from the spectrum subtraction;

wherein the step of blood predicting the glucose concentration further comprises; comparing the spectrum subtraction of the unknown glucose concentration with a plurality of sample spectrum subtractions which are obtained from a living body whose blood glucose concentration is known in a similar manner as obtained from the living body whose blood glucose concentration is unknown and predicting the blood glucose concentration of the unknown constituents blood.

Further, in the blood glucose concentration predicting steps according to the embodiment of the present invention, the blood constituent predicting step further includes steps of preparing a multi-regression analyzing model, into which spectrum data of plural whole blood samples having known blood constituent is input as an explanatory variable and blood constituent is output as an objective variable, inputting the spectrum subtraction data obtained from blood of which blood constituent is not known as an explanatory variable, and outputting the blood constituent as an objective variable.

BRIEF DESCRIPTION OF THE DRAWINGS

FIG. 11 is a diagram for explaining the operation of a blood glucose prediction instrument shown in FIG. 8.

DETAILED DESCRIPTION OF THE INVENTION

An embodiment of the present invention will be described below in detail referring to the attached drawings. In the embodiment shown below, the measurement of blood glucose concentration as blood constituent will be explained. However, the present invention is also applicable to the measurement of concentration of other materials that are blood constituents other than blood glucose existing in the arterial having light absorption characteristic and scattering as well as reflecting characteristic.

Figure 1:
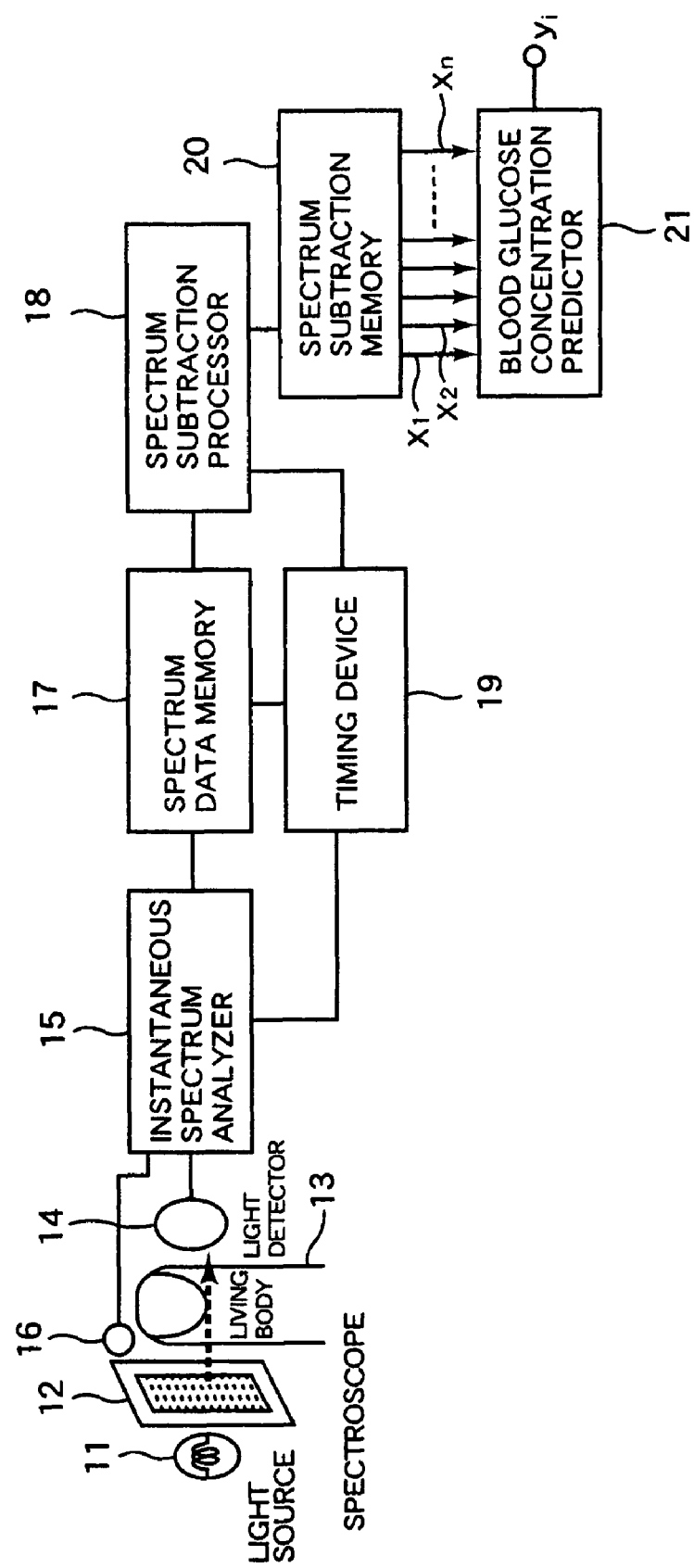
FIG. 1 is a block diagram showing a structure of a non-invasive blood constituent measuring instrument according to a first embodiment of the present invention.

FIG. 1 is a block diagram showing a first embodiment of a non-invasive blood glucose concentration measuring instrument according to the present invention.

As shown in FIG. 1, the light source 11 to emit a light having a near infrared wavelength range of, for example, 800-2400 nm wavelength has been installed in a non-invasive blood glucose concentration measuring instrument. The light emitted from the light source 11 is irradiated to a living body 13 such as a fingertip, an ear lobule, etc. through an active spectroscope 12. The active spectroscope 12 separates light emitted from the light source 11 sequentially over its whole wavelength range at an interval of, for example, 3 nm and sequentially outputs about 530 number of lights having a different wavelength. The scanning of the wavelength by the active spectroscope 12 in the above-mentioned wavelength range is executed repeatedly about 20 times in one cycle time of arterial waveform in the living body 13. In other words, the active spectroscope 12 transmits the lights in a near infrared range sequentially at an interval of about 50 ms and irradiates them to the living body 13. The light passed through the living body 13 is received by a light receiver arranged at the opposite side of the light source 11 and is converted into an electric signal. Here, the scanning of the wavelength by the active spectroscope in the above-mentioned wavelength range is executed repeatedly for example about 20 times in one cycle time of the arterial volume waveform in the living body 13, however, it is not limited to 20 times, but it may be repeated more than 20 times.

An output signal of the light receiver 14 is supplied to a spectrum analyzer 15, wherein an absorption spectrum obtained as an output of the light receiver 14 for each wavelength of the light source 11 is produced. That is, the output from a sensor 16 that detects an intensity of the light incident to the living body 13 from the light source 11, that is, an intensity of the incident light Io is supplied with the output signal of the light receiver 14 to the spectrum analyzer 15. As described later, the intensity of light of each wavelength λ passed through the living body 13, that is, an absorbance which is a ratio of the intensity of passed light I to the intensity of the incident light Io (I/Io) is computed here and an absorption spectrum is produced. Twenty (20) number of the absorption spectrums are produced per second by twenty (20) times of scanning per second of the active spectroscope 12 as described above.

The absorption spectrum data obtained by the spectrum analyzer 15 is stored in a spectrum data memory 17. The spectrum data memory 17 stores and maintains output data for several seconds of the spectrum analyzer 15 sequentially in the first-in first-out basis.

Spectrum data read from the spectrum data memory 17 is supplied to a subtraction processor 18 and a spectrum subtraction, which is composed of a difference in absorbance in corresponding wavelengths between absorption spectrums at different times is produced as described later.

The spectrum analyzer 15, the spectrum data memory 17 and the subtraction processor 18 are operated in sync with the 20 times scanning per second of the active analyzer 12. The synchronization between these units is made by a timing device 19 to supply a synchronizing signal to them.

The spectrum subtraction data produced by the subtraction processor 18 is stored in a spectrum subtraction memory 20. The spectrum subtraction memory 20 also stores the output data of the subtraction processor 18 for several seconds sequentially in the first-in first-out basis.

The spectrum subtraction data read out of this spectrum subtraction memory 20 is input into a blood glucose predictor 21. The blood glucose predictor 21 is a device to predict blood glucose concentration through the multi-regression analysis using the PLS (Partial Least Squares Regression) method that is one of multi-regression analyses from input spectrum subtraction data. That is, the blood glucose predictor 21 is constructed as a software model to compute the blood glucose concentration according to the PLS method using whole blood samples that have many known blood glucose concentrations.

Figure 2:
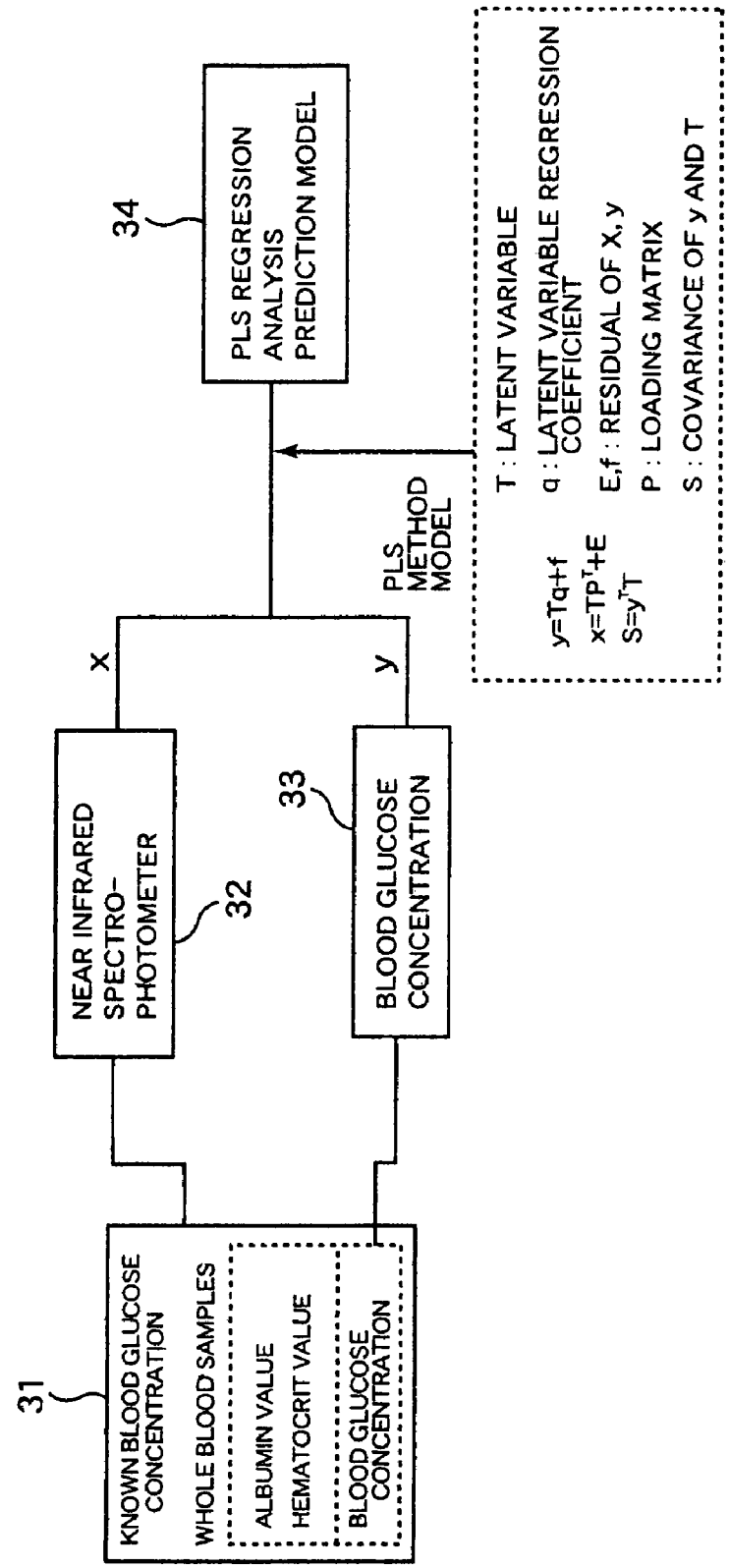
FIG. 2 is a flowchart showing a construction method of an analytical prediction model used in the blood glucose concentration prediction instrument shown in FIG. 1.

FIG. 2 is a flow chart showing a method for constructing the blood glucose predictor 21 as the software model shown in FIG. 1. Known blood glucose concentration samples 31 are bloods filled in plural quartz photo-cells (not illustrated) whose glucose concentrations are known and are slightly different from each other. These samples 31 were taken directly from, for example, seven healthy adult males and were made plural whole bloods having different albumin or hematocrit concentrations from other bloods by 18 mg/dl like 36, 54, . . . , 486 mg/dl in the glucose concentration range 30-450 mg/dl. These samples 31 are analyzed by a spectroscopic analyzer composed of the light source 11, the spectroscope 12, the light receiver 14 and the spectrum analyzer 15, and thus an absorption spectrum 32 is prepared. A PLS regression analysis prediction model 34 is decided by data X consisting of these absorption spectrum 32, together with corresponding known n number of blood glucose concentrations (yn) 33. That is, data X consisting of the absorption spectrum 32 is an absorbance for different m (about 530 waves) number of the spectroscopic waveforms. Expressing these absorbance with $x_1, x_2, \ldots, x_m$, the known n number of blood glucose concentrations y1, y2, . . . , yn are approximated by the following determinant using these variables:

$$\begin{bmatrix} y1 \\ y2 \\ \\ yn \end{bmatrix} = \begin{bmatrix} a11 & \ldots & a1n \\ & & \\ a1n & \ldots & ann \end{bmatrix} \begin{bmatrix} X1 \\ X2 \\ \\ Xn \end{bmatrix} \quad \text{Formula 1}$$

A coefficient of this determinant is decided using the PLS method by substituting the absorption spectrum data using the above-mentioned sample solution into the determinant. A blood glucose prediction model formula is thus obtained. Here, the PLS method is a technique to consider the correlation of potential variables $T_{PLS}$ as explanatory variables and to utilize data contained in X as many as possible.

$$\left. \begin{aligned} y &= Tq + f \\ X &= TPt + E \\ S &= ytT \end{aligned} \right\} \quad \text{Formula 2}$$

where,
T: Potential variable
q: Potential variable regression coefficient
E,f: Residual of X, y
P: Loading matrix
S: Covariance of y and T P of the determinant 2 and regression coefficient q of potential variable T are decided by inputting blood glucose $y_1$, $y_2, \ldots y_n$ of n known blood glucose samples into a regression analytical computer application software (for example, Trade Name: MATLAB) according to the PLS method available in the market. Thus, the regression analysis prediction model (blood glucose computing model) according to the PLS method is obtained. Then, a new T is computed based on P that is decided when a model is prepared, when new absorbance of respective spectroscopic wavelengths $x_1, x_2, \ldots, x_m$ obtained from blood of which blood glucose concentration is unknown are input as data. These new absorbance of respective spectroscopic wavelengths $x_1, x_2, \ldots, x_m$ are input as spectrum subtraction data read from the above-mentioned spectrum subtraction memory 20. Using this new T and q decided when a model was prepared, a blood glucose prediction value $y_i$ is obtained.

Next, the operations of the non-invasive blood glucose concentration measuring instrument thus constructed according to the embodiment of the present invention and the blood glucose measuring procedures will be explained referring to FIG. 3 and FIG. 4.

As shown in FIG. 1, the light emitted from the light source 11 is spectroscopically scanned over the wavelength range by the active spectroscope 12 at a rate of 20 times per second and is irradiated to the living body 13. The light transmitted through the living body 13 is received by the light receiver 14 and each absorption spectrum is measured by the spectrum analyzer 15 at an intervals of 40-50 ms. The spectrum data thus measured is stored in the spectrum memory 20 until the next spectrum measuring time. FIG. 3 shows the arterial pulsatile waveform in the living body 13, the horizontal axis shows time and the vertical axis shows arterial blood flow (pulsatile waveform). Time $t_1, t_2, \ldots, t_n$ in FIG. 3 show the time when the scanning of the wavelength starts by the active spectroscope 12, where n is 20. Absorption spectrum at the time $t_1, t_2, \ldots, t_n$ thus obtained are shown in FIG. 4, where the horizontal axis shows wavelength and the vertical axis shows absorbance.

Next, the spectrum subtraction processor 18 shown in FIG. 1 produces a spectrum subtraction from absorption spectrums at two optional times, for example, a time $t_1$ and a peak time $t_i$ in the arterial pulsatile waveform selected from the times $t_1, t_2, \ldots, t_n$.

Figure 5:
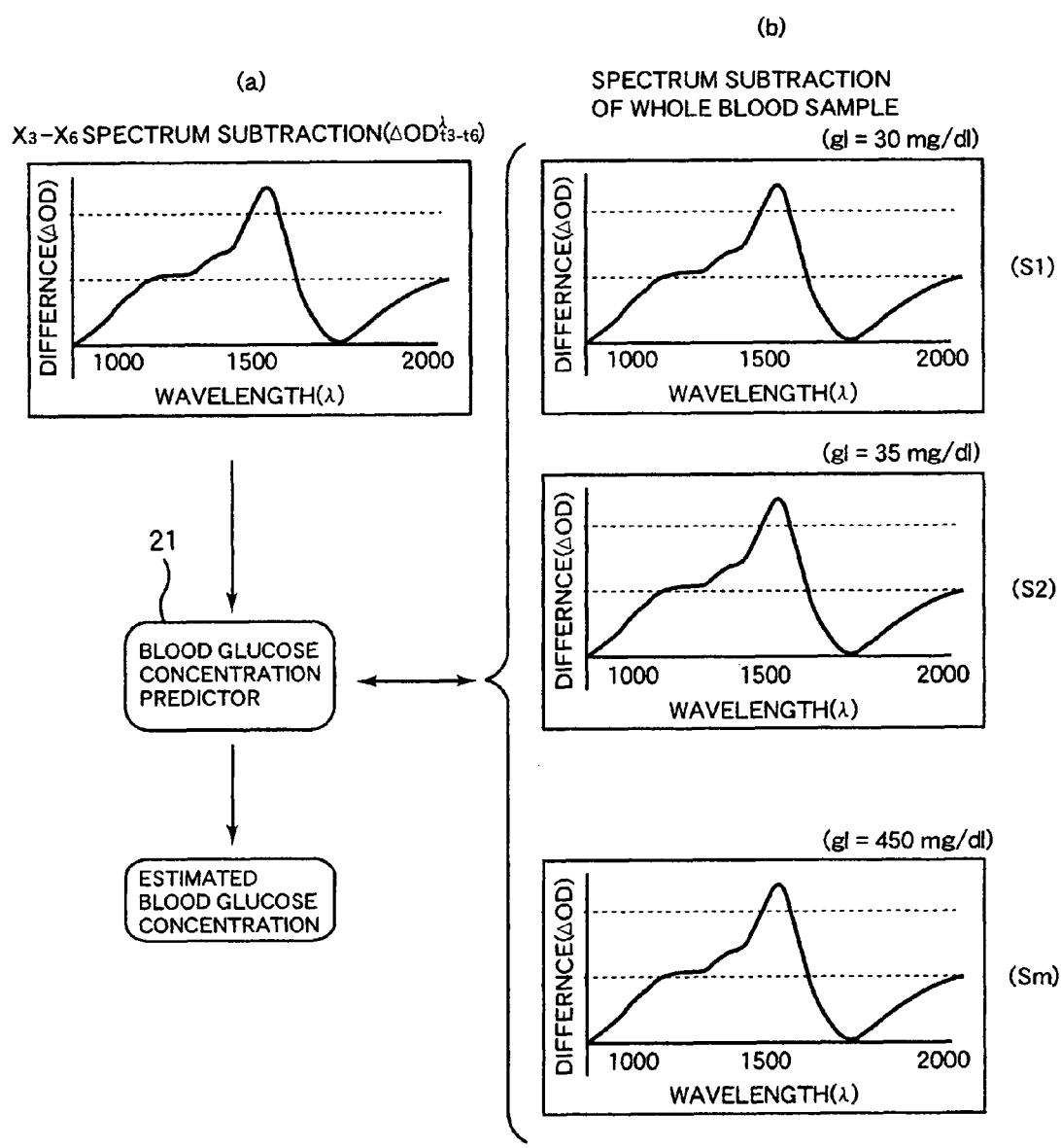
FIG. 5 is a diagram for explaining the operation of a blood glucose prediction instrument shown in FIG. 1.

FIG. 5 is a diagram for explaining an operation of the blood glucose predictor 21 shown in FIG. 1. One example of the above-mentioned spectrum subtraction is shown in FIG. 5(a). The horizontal axis in FIG. 5 shows wavelength and the vertical axis shows a difference in the absorbance. The curved line indicating the spectrum subtraction is a plotted difference in the absorbance at respective wavelengths of absorption spectrum at $t_3$ and $t_6$. The calculation is done using the formula;

$$\log(\text{transmitted spectrum at } t=t3) - \log(\text{transmitted spectrum at } t=t6) = \log((\text{transmitted spectrum at } t=t3)/(\text{transmitted spectrum at } t=t6)).$$

Graphs (S1), (S2), ..., (Sm) in FIG. 5(b) show absorption spectrums of m number of whole blood samples of known blood glucose concentration.

Spectrum subtraction data shown in FIG. 5(a) are input to the blood glucose concentration predictor 21. Further, a PLS regression analytical model is incorporated in the blood glucose concentration predictor 21. The PLS regression analytical model is a numerical expression showing the relation between absorption spectrums of m number of whole blood samples (S1), (S2), ..., (Sm) shown in FIG. 5 each having known blood glucose concentration and the known blood glucose concentrations corresponding to the samples. The blood glucose concentration predictor 21 compares the spectrum subtraction given from the spectrum subtraction memory 20 as input data with each of the absorption spectrums of the sample solutions and outputs the blood glucose concentration of the sample solution having most similar absorption spectrum as a predicted blood glucose concentration.

Figure 6:
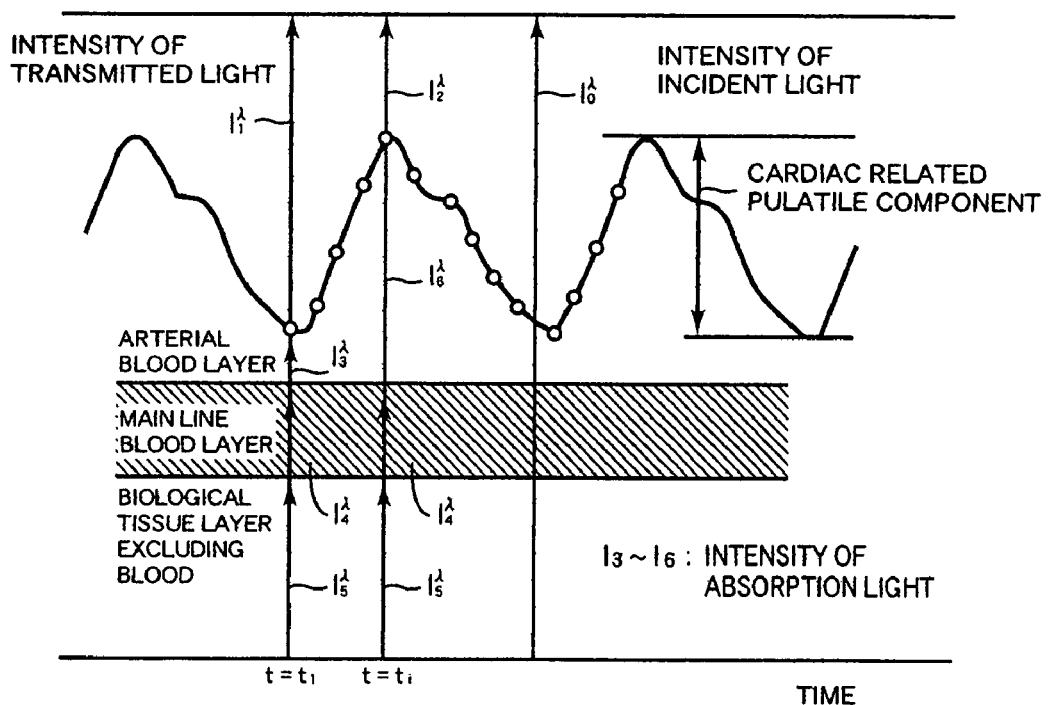
FIG. 6 is a diagram showing properties of the light passed through a living body for explaining the principle of the present invention.

Thus, it was revealed that a blood glucose concentration can be predicted at a high level of accuracy when spectrum subtraction is used as input data to the blood glucose concentration predictor 21. The reason will be explained referring to FIG. 6. FIG. 6 is a typical diagram showing the relation of the intensity of incident light $I_O$, the intensities of transmitted lights $I_1, I_2$ and absorption amount in the living body 13. The arterial blood waveform P shown in FIG. 4 is also shown in FIG. 6. In FIG. 6, for example, the transmitted light intensity $I_1$ (Incident light intensity $I_O$) at $t=t_1$ where the arterial blood waveform P becomes minimum is (Incident light intensity $I_O$)−(Absorption light intensity in arterial blood layer at the minimum flow rate $I_3$)−(Absorption light intensity in venous blood layer $I_4$)−(Absorption light intensity in biological tissues other than blood $I_5$). Further, the transmitted light intensity $I_2$ at $t=t_2$ where the flow rate in the arterial becomes the maximum is (Incident light intensity $I_O$)−(Absorption light intensity in arterial blood layer of the minimum flow rate $I_6$)−(Absorption light intensity $I_4$)−(Absorption light intensity in biological tissues other than blood $I_5$). The differences of these two spectrums extract spectrum of pulsative element $\Delta I$ that is pulsating absorption intensity of the artery with commonly included absorption light intensity I in the biological tissues other than blood commonly removed. Accordingly, the absorption light spectrum in the spectrum analyzer 15 or the spectrum data memory 17 shown in FIG. 1 contains the absorption light element in the venous blood and biological tissues other than blood. However, spectrum subtraction generated in the spectrum subtraction processor 18 becomes light absorption spectrum depending on light absorption element of arterial blood absorption element only. Accordingly, this spectrum subtraction does not contain the absorption element by the venous blood and biological tissues other than blood. Therefore, it becomes possible to eliminate influence of these interfering factors and to put into practical use of a highly precise non-invasive blood glucose concentration measuring instrument.

By the way, in producing spectrum subtraction by the measurement of living body 13 described above, when a difference in arterial spectrum waveforms that become the maximum and minimum flow rates in one heart beat, the blood glucose concentration is computed at one time per one heart beat and the blood glucose concentration is output at one time per one heart beat. However, as spectrum data is measured repetitively nearly 20 times in one heart beat, it is possible to take out spectrum subtraction at two adjacent times as continuous spectrum subtractions while shifting times sequentially and compute blood glucose concentrations using these continuous spectrum subtractions. In this case, it is expected that a change in spectrums at adjacent times is very little, signal noise ratio of spectrum subtraction drops and a fluctuation (a residual error) of the result of blood glucose concentration computation may become large. Accordingly, it is also possible to display the measured result easy to look by inputting the result into the blood glucose concentration predictor 21 by executing the time series average of these spectrum subtractions or by smoothing successively computed blood glucose concentrations through the statistical procedure such as the time average or moving average by the blood glucose concentration predictor 21.

Further, in the embodiment described above, the transmitted light spectrum from the living body 13 is measured but the reflected light from the living body 13 may be measured other than the transmitted light.

Figure 7:
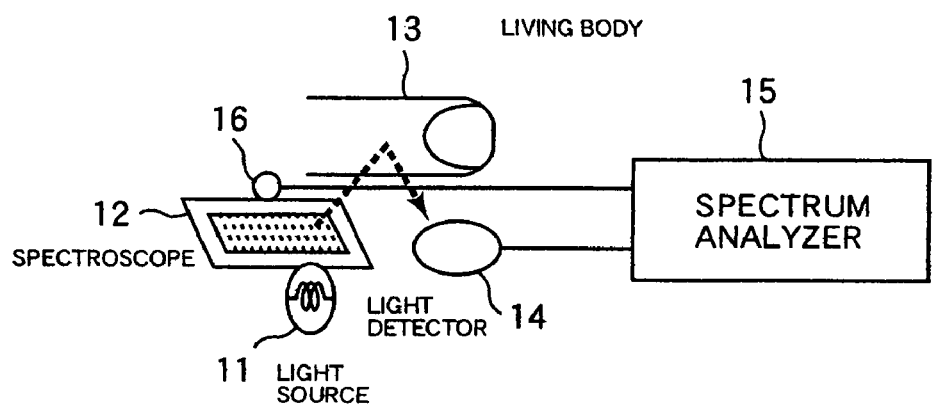
FIG. 7 is a diagram showing a second embodiment of the non-invasive blood glucose concentration measuring instrument according to the present invention.

FIG. 7 is a partial explanatory diagram showing this embodiment, in which the same constituent elements as those in FIG. 1 are assigned with the same reference numerals and the detailed explanation thereof will be omitted. In this embodiment, the light receiver 13 is arranged at the same side as the light source 11 to the living body 13 as illustrated and receives the reflected light from the living body 13. By supplying the output signal of the light receiver 13 to the spectrum analyzer 15 shown in FIG. 1, it is possible to measure a blood glucose concentration likewise the embodiment described above.

Further, in the embodiments shown in FIG. 1 and FIG. 7, the light from the light source 11 is separated by the active spectroscope 12 and then irradiated to the living body 13. However, the transmitted light or reflected scattering light may be separated for spectrum analysis after the light from the light source 11 is irradiated to the living body 12. For example, the light can be separated by an array of plural light receivers each having a sensitivity only for specific wavelengths ($\lambda$).

Figure 8:
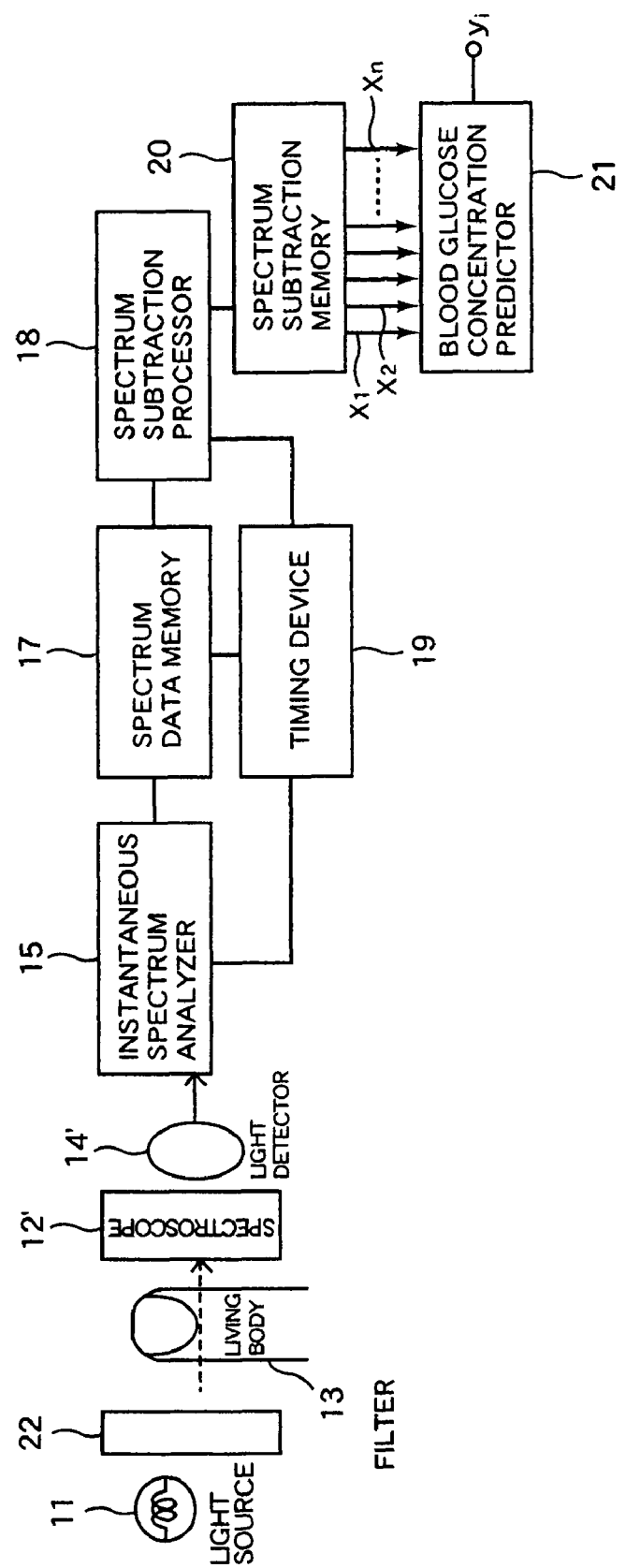
FIG. 8 is a block diagram showing a structure of a non-invasive blood glucose concentration measuring instrument which is a third embodiment of the present invention.

FIG. 8 is a block diagram showing a second embodiment of a blood glucose prediction instrument using an instrument of the kind. In FIG. 8, the same constituent elements as those in the first embodiment shown in FIG. 1 are assigned with the same reference numerals and the detailed explanation thereof will be omitted to avoid duplication. Hereinafter the explanation will be limited only to different portions.

The light emitted from the light source 11 is irradiated to the living body 13 through the filter 22 which transmits the light near infrared range only. The light transmitted through the living body 13 is separated by an active spectroscope 12' arranged on the opposite side to the light source 11. The active spectroscope 12' separates light passed through the living body 13 over the range of wavelength at an interval of, for example, 3 nm and sequentially outputs about 530 number of lights having different wavelengths. A light detector 14' is composed of an arrangement of a number of detectors having sensitivity for a light of a specific wavelength, for example, wave lengths in the range of 3 nm wide. The light detector 14' scans over whole range of the wavelength in about of 8 ms of exposure time by measuring and reading out of light intensity. In a blood glucose predictor 21', a regression analysis prediction model is used, which is constructed by a different method from that used in the first embodiment.

Figure 9:
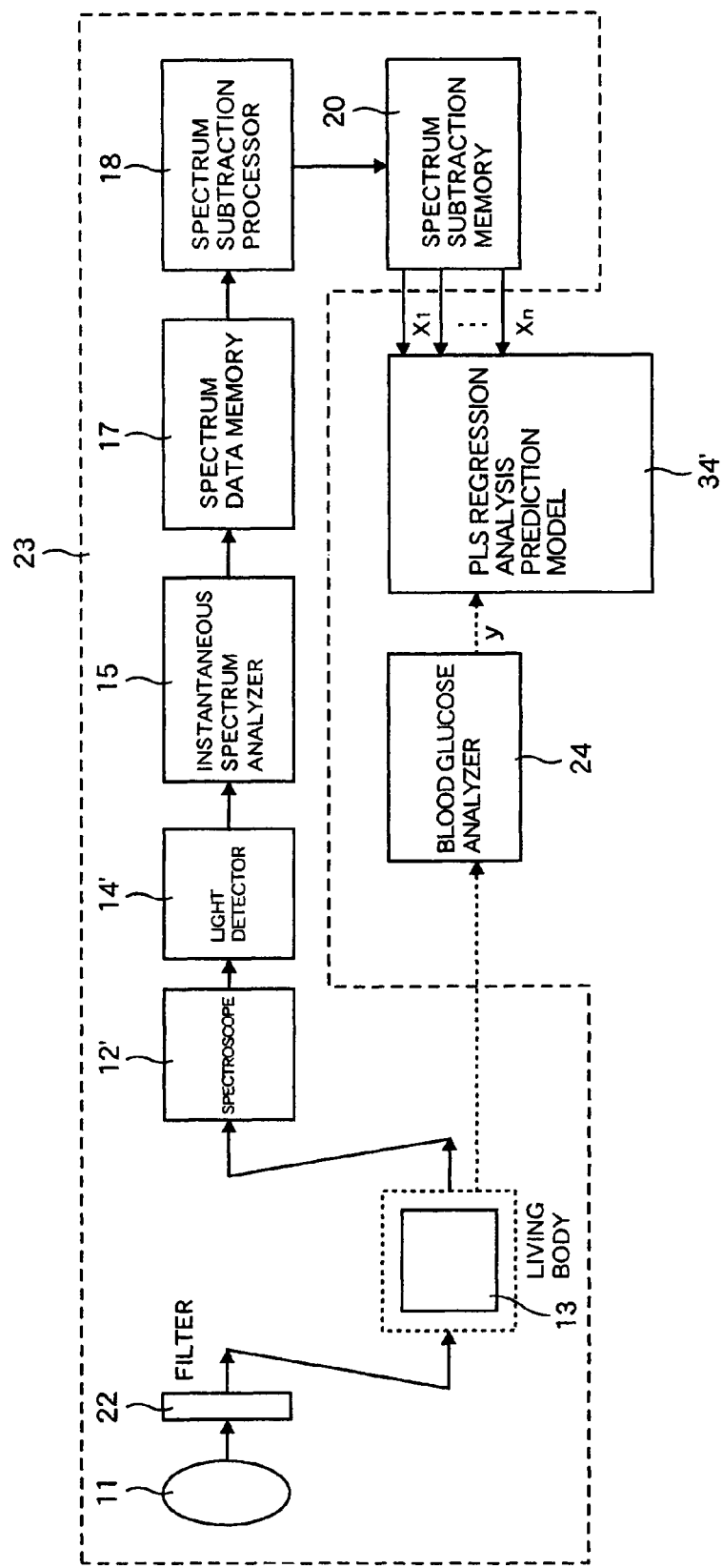
FIG. 9 is a flowchart showing a construction method of an analytical prediction model used in the blood glucose concentration prediction instrument shown in FIG. 8.

FIG. 9 is a block diagram for explaining the construction method for the regression analysis prediction model contained in the blood glucose predictor 21'. In FIG. 9, the same constituent elements as those in FIG. 8 are assigned with the same reference numerals and the detailed explanation thereof will be omitted to avoid duplication. Hereinafter the explanation will be limited only to different portions.

The block surrounded with a dotted line in the figure is a sample spectrum subtraction measuring instrument 23. The instrument 23 includes the light source 11, near infrared transmitting filter 22, the living body 13, the active spectroscope 12', the light detector 14', the spectrum analyzer 15, a sensor portion 16, the spectrum data memory 17, the subtraction processor 18, the timing device 19, and the spectrum subtraction memory 20. The instrument 23 is similar with the elements included in the blood glucose prediction instrument in FIG. 8, so that the same elements in FIG. 9 are assigned with the same reference numerals in FIG. 8. In the method shown in FIG. 9, a blood glucose analyzer 24 is used for measuring the blood glucose concentration of the blood taken from the living body 13.

In this model construction method, a number of 27 healthy trial subjects, for example, were subject to glucose tolerance test, in which test solution is given orally and spectrum measurement by the sample spectrum subtraction measuring instrument and blood glucose concentration measurement by blood taken from the trial subjects were carried out for a period of 120 minutes with 5-10 minutes interval from the time the test solution is given, to obtain as many blood glucose concentration samples as possible in the glucose density range 30-450 mg/dl. At this time, it is desirable to obtain as wider range samples as possible for the albumin concentration or hematocrit concentration in the blood.

More specifically, a light from the light source 11 is irradiated on the living body 13 which is a finger of the trial subjects through the near infrared transmitting filter 22, and the light transmitted through the finger is detected as electric signals at each wavelength by the active spectroscope 12' and the light detector 14'. The output signal of the light detector 14' is supplied to the spectrum analyzer 15, and a transmitted light spectrum is formed, which consists of output signals of each wavelength of the light detector 14'. That is, in the spectrum analyzer 15, 125 transmitted light spectrums per second are produced by the sampling of the light detector 14 at every exposure time of about 8 ms.

The transmitted light data obtained by the spectrum analyzer 15 are stored in a spectrum data memory 17 until the next spectrum measuring timing. This spectrum data memory 17 stores and maintains output data for several seconds of the spectrum analyzer 15 sequentially on the first-in first-out basis.

The spectrum data read out from the spectrum data memory 17 are supplied to the subtraction processor 18, and sample light absorption subtraction spectrums are obtained by subtraction calculation between transmitted light spectrums of the different time having a corresponding wavelength, as will be mentioned later.

Here, the spectrum analyzer 16, the spectrum data memory 17, and the subtraction processor 18 operate in synchronization with the output scanning of the light detector 14' at a rate of 125 times per second.

Figure 10:
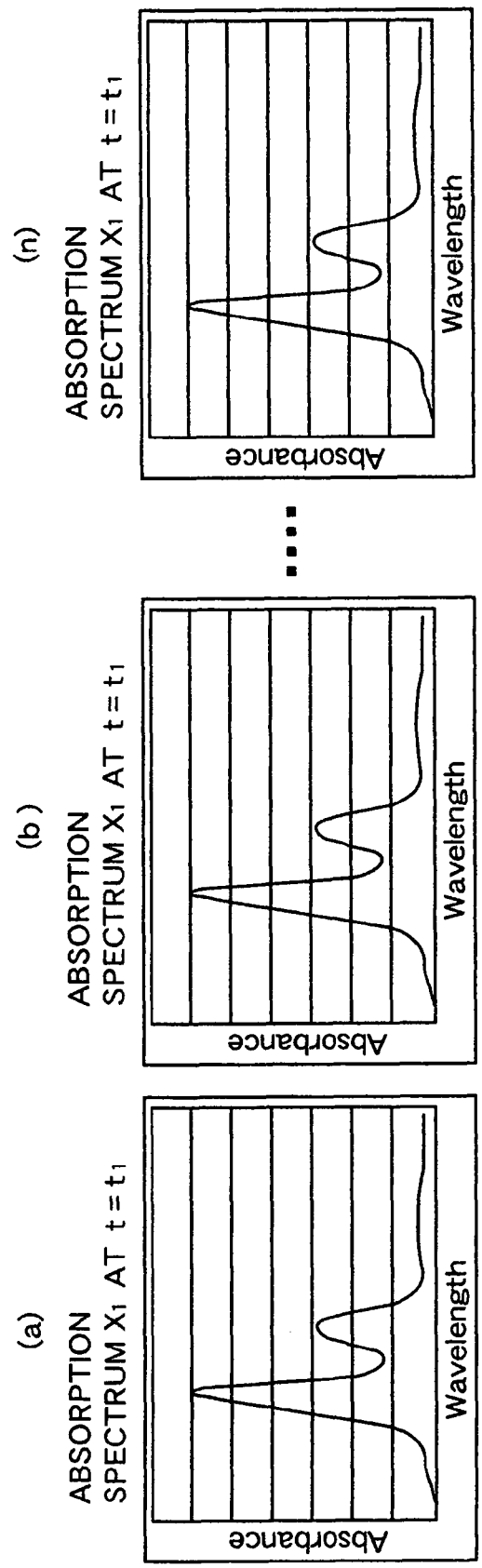
FIG. 10 is a waveform diagram showing examples of spectrums output from a spectrum analyzer in FIG. 9.

The sample light absorption subtraction spectrum data obtained from the subtraction processor 18 are stored in the spectrum subtraction memory 20. This spectrum subtraction memory 20 also stores and maintains the output data of the subtraction processor 18 for several seconds sequentially on the first-in first-out basis. In this spectrum data memory 17, the transmitted light spectrum at $t=t1, t2, \ldots, tn$ in pulsatile arterial volume waveform of the living body shown in FIG. 3 are stored. The transmitted light spectrums at each time $t=t1, t2, \ldots, tn$ obtained in this way are shown in FIG. 10. The horizontal axis in the figure indicates wavelength, the vertical axis indicates transmitted light intensity.

Figure 3:
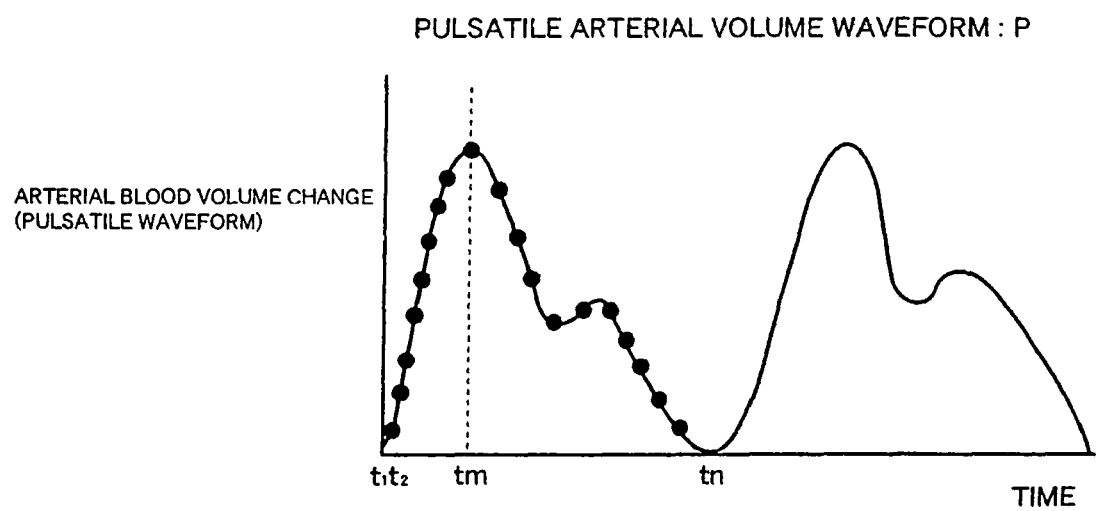
FIG. 3 is a diagram showing an arterial pulsatile waveform in a living body.
Figure 4:
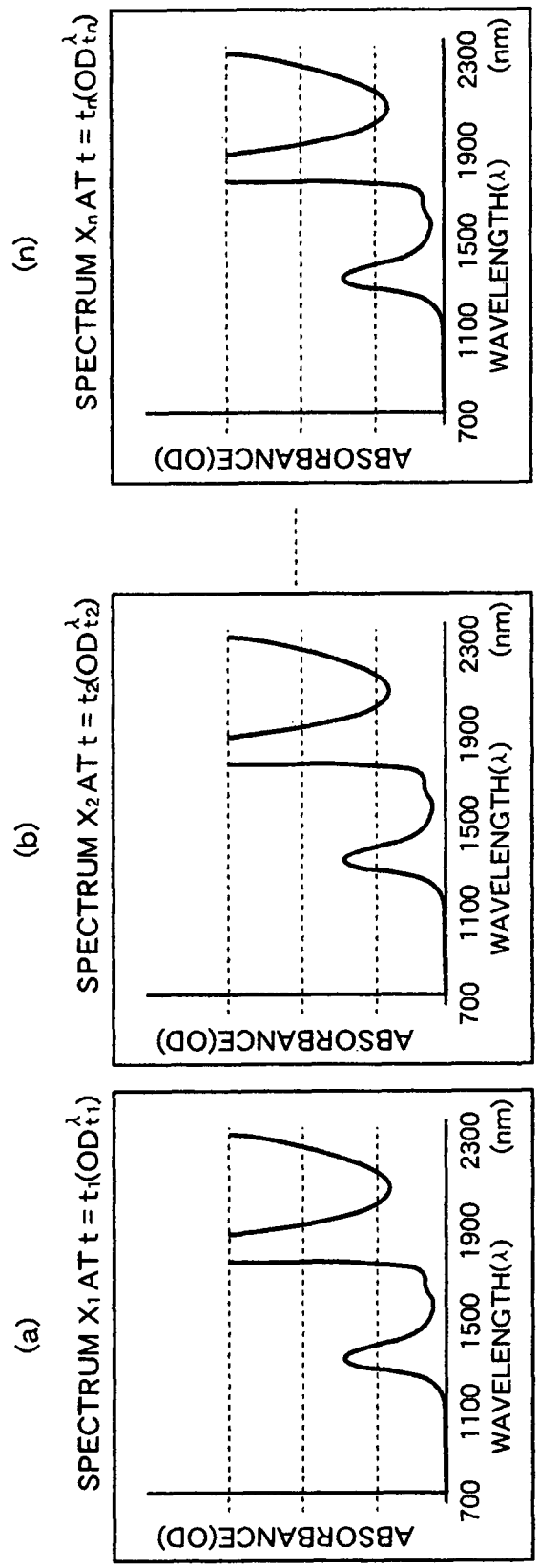
FIG. 4 is a waveform diagram showing examples of spectrums output from a spectrum analyzer in FIG. 1.

Next, the subtraction processor 18 shown in FIG. 9 produces sample subtraction absorption spectrum data (x1, x2, . . . , xn) from the absorption spectrums at each time $t=t1, t2, \ldots, tn$ in FIG. 3 read out from the spectrum data memory 17 at arbitrary two different times, for example, rise time of arterial blood waveform t1, and the peak time tj, and these are stored in the spectrum subtraction memory 20.

This subtraction absorption spectrum can be obtained from absorption intensity spectrums at arbitrary two different times, and is given by the following formula;

subtraction absorption spectrum=log(transmission light spectrum at $t=t1$)−log(transmission light spectrum at $t=t2$)=log((transmission light spectrum at $t=t1$)/(transmission light spectrum at $t=t2$)).

A PLS regression analysis prediction model 34' is constructed from the sample subtraction absorption spectrum data (x1, x2, . . . , xn) read out by the spectrum subtraction memory 20 and from the output data y of the blood glucose concentration analyzer 24. This PLS regression analysis prediction model 34' is a software model for predicting a blood glucose concentration by utilizing a PLS method, one of multivariate analysis.

FIG. 11 is a diagram for explaining the operation of the blood glucose prediction instrument shown in FIG. 8. In FIG. 11 (*a*), an example of sample subtraction absorption spectrum data is shown, which is measured from a living body whose blood glucose concentration is unknown using an instrument shown in FIG. 8. The horizontal axis of the figure indicates wavelength, the vertical axis indicates the difference of absorption. The curves in the graph showing the subtraction absorption spectrum are made by plotting the absorption difference at each wavelength of each absorption spectrum at t=t3 and t=t6. In FIG. 11 (b), (S1), (S2), . . . , (Sm) are examples of m number of subtraction absorption spectrums obtained from the light transmitted through the trial subjects whose blood glucose concentrations are known.

In the blood glucose concentration predictor 21' shown in FIG. 8, sample subtraction absorption spectrum data shown in FIG. 11 (a) is input. In the blood glucose concentration predictor 21', a PLS regression analysis prediction model is built in, which is a mathematical formula showing a relation between m number of subtraction absorption spectrums (S1), (S2), . . . , (Sm) obtained from trial subjects whose blood glucose concentrations are known and the corresponding blood glucose concentrations.

The blood glucose concentration predictor 21' compares the subtraction absorption spectrum supplied as input data from spectrum subtraction memory 20 with the absorption spectrums (S1), (S2), . . . , (Sm), and outputs the blood glucose concentration of the absorption spectrum having a most similar absorption spectrum as an estimated blood glucose concentration.

Here, the m number of subtraction absorption spectrums (S1), (S2), . . . , (Sm) are different from the sample spectrums obtained from the whole blood shown in FIG. 5. That is, in the spectrum shown in FIG. 5, absorption by water in 1400 nm to 1500 nm wavelength range is observed, however, such absorption spectrum by water is not observed in the spectrum shown in FIG. 11. It was experimentally confirmed that the reason is because the spectrum shown in FIG. 5 is obtained by optically measuring a blood sample taken from a living body and filled in quartz photo-cells using the instrument shown in FIG. 1. On the other hand, the spectrum shown in FIG. 11 (b) was obtained by optically measuring the blood in the living body with non-invasively.

A more precise prediction of blood glucose concentration compared with the first embodiment becomes possible by using a subtraction spectrum obtained by non-invasively measuring a living body whose blood glucose concentration is known, as an absorption spectrum sample whose blood glucose concentration is known for constructing the PLS regression analysis prediction model, because such an unwanted spectrum component as an absorption by water, for example, is eliminated which is observed in sample absorption spectrum using whole blood sample.

Further, in the embodiments described above, a model applied with the PLS method was used as the blood glucose concentration predictor 21. However, a model according to the Principal Components Regression method (hereinafter referred to as PCR method) shown in Formula 3, which is one of multi-regression analysis may be used. The regression analysis blood glucose concentration computing model that is constructed using the PCR method is expressed by the following Formula 3.

$$\left. \begin{array}{l} Y = Tb + f \\ = t_1 b_1 + t_2 b_2 + \ldots + t_n b_n \end{array} \right\} \quad \text{Formula 3}$$

where, T: Principal constituents score b: Principal constituents score regression coefficient That is, a multi-regression analysis blood glucose concentration computing model is constructed by corresponding a known blood glucose concentration of the whole blood sample 31 to an objective variable y, applying spectrum data of the whole blood sample 31 to an explanatory variable x and deciding a multi-regression analysis blood glucose concentration computing model. When spectrum subtraction data of an unknown blood glucose concentration is input into the blood glucose concentration predictor 21 in which this principal constituents score regression coefficient b is set, a blood glucose concentration predict value ya is computed and output.

Further, in the construction method of an regression analysis prediction model shown in FIG. 9, the sample spectrum subtraction measuring instrument 23 shown in FIG. 8 is used for making a sample subtraction spectrum from a living body whose blood glucose concentration is known. However, it is needless to say, the sample subtraction spectrum analyzer shown in FIG. 1 having a substantially same construction may be used.

Further, in the embodiment mentioned above, the measurement of blood glucose concentration is shown. However, regarding the measurement of concentration of another material having absorption characteristic and scatter reflection characteristic existing in the arterial blood, it is possible to predict and compute the concentration of that material existing in the arterial blood similarly. That is, it is possible to predict and compute the concentration by measuring spectrum of wavelength band corresponding to the absorption characteristic or the reflecting characteristic of the material and deciding the regression coefficient of the multi-regression analyzing model using the PLS method or the PCR method referring to a concentration of a sample of that is the standard of that material using the same system and procedures shown in the above embodiment.

As described above, with the non-invasive blood constituent measuring instrument and the method according to the embodiment of the present invention, it is possible to measure blood constituents of blood in a living body by irradiating near infrared light to a finger tip, etc. quickly and highly precisely without feeling pain and burden involved in the blood drawing.

Further, according to the embodiment of the present invention, spectrum subtraction using the arterial blood beat is used as described above. However, the spectrum subtraction analysis may be made by generating the blood pulsation change in the biological tissues using such a method as the blue pipe pressing method, for example. Thus, the adverse effect of other biological tissue constituents is eliminated and blood constituent can be measured at a highly precise and sensitive level.

What is claimed is:

1. A non-invasive blood constituents measuring instrument comprising: a light source for irradiating light in the near infrared range including plural wavelengths to a living body whose blood constituent concentrations are unknown; a light receiver to detect light transmitted through the living body or reflected therefrom; an active spectroscope for separating the light into plural wavelengths in the near infrared range at an interval of 40-50 ms period of time; a spectrum analyzer to which the output signal of the light receiver is supplied and which analyzes spectrum of the light transmitted through the living body or reflected therefrom at different times having a shorter time intervals than a cycle time of the arterial waveform cycle; a spectrum subtraction generator to generate a plurality of spectrum subtractions from the spectrum of the light measured by the spectrum analyzer at any two different times corresponding to time intervals of 40-50 ms; and a blood constituent concentrations predictor into which the output data of the spectrum subtraction generator is input and which outputs the blood constituent concentrations, wherein the blood constituent concentrations predictor comprises a multi-regression analyzing model;

wherein the multi-regression analyzing model is calibrated by supplying plural sample data comprising spectrum subtractions obtained non-invasively from a living body having known blood constituent concentrations as explanatory variables and the known blood constituent concentrations as objective variables, using the non-invasive blood constituents measuring instrument;

wherein the output data of the spectrum subtraction generator obtained from the living body whose blood constituent concentrations are unknown is input to the blood constituent concentrations predictor and the blood constituent concentrations predictor outputs the blood constituent concentrations calculated by the calibrated multi-regression analyzing model.

2. A non-invasive blood constituents measuring instrument claimed in claim 1, wherein the multi-regression analyzing model is a regression analysis model using the PLS or PCR method.

3. A non-invasive blood constituent measuring instrument claimed in claim 2, wherein blood constituent concentrations of the living bodies corresponding to the sample spectrum subtractions are arranged at a specified interval within a range of concentration including a physiological concentration range.

4. A non-invasive blood constituent measuring instrument claimed in claim 1, wherein the light includes plural wavelengths in the wavelength band of 800-2400 nm arranged at an interval of 3 nm.

5. A non-invasive blood glucose concentration measuring instrument comprising: a light source to irradiate a light in the near infrared range containing plural wavelengths to a living body whose blood glucose concentration is unknown; a light receiver to detect the light transmitted through a living body or reflected therefrom; an active spectroscope for separating the light into plural wavelengths in the near infrared range at an interval of 40-50 ms period of time; a spectrum analyzer to which the output signal of the light receiver is supplied and which analyzes spectrum of the light transmitted through the living body or reflected therefrom at different times having a shorter time intervals than a cycle time of the arterial waveform; a spectrum subtraction generator to generate a plurality of spectrum subtractions from the spectrum of the light measured by the spectrum analyzer at any two different times corresponding to time intervals of 40-50 ms; and a blood glucose concentration predictor into which the output data of the spectrum subtraction generator is input and which outputs the blood glucose concentration, wherein the blood glucose concentration predictor comprises a multi-regression analyzing model;

wherein the multi-regression analyzing model is calibrated by supplying plural sample data comprising spectrum subtractions obtained non-invasively from a living body having known blood glucose concentrations as explanatory variables and the known blood glucose concentrations as objective variables, using the non-invasive blood glucose concentration measuring instrument; and wherein the output data of the spectrum subtraction generator obtained from the living body whose blood glucose concentrations are unknown is input to the blood glucose concentrations predictor model and the blood glucose concentrations predictor outputs the blood glucose concentrations calculated by the calibrated multi-regression analyzing model.

6. A non-invasive blood glucose concentration measuring instrument claimed in claim 5, wherein the multi-regression analyzing model is a regression analysis model using the PLS or PCR method.

7. A non-invasive blood glucose concentration measuring instrument claimed in claim 6, wherein blood glucose concentrations according to the sample spectrum subtractions are arranged at a specified interval within a range of concentration including a physiological concentration range.

8. A non-invasive blood glucose concentration measuring instrument claimed in claim 5, wherein the light includes plural wavelengths in the wavelength band of 800-2400 nm arranged at an interval of 3 nm.

9. A method for non-invasively measuring blood constituents comprising the steps of: irradiating a light in the near infrared range containing plural wavelengths to a living body whose blood constituents are unknown; detecting light transmitted through or reflected from the living body and converting it into an electric signal; separating the light into plural wavelengths in the near infrared range at an interval of 40-50 ms period of time; analyzing spectrum of the light transmitted through the living body or reflected therefrom at different times having a shorter time intervals than a cycle time of the arterial waveform cycle using the converted electric signal; generating a plurality of spectrum subtractions from the spectrum of the light measured by the spectrum analyzer at any two different times corresponding to time intervals of 40-50 ms; and predicting corresponding blood constituents concentration from the spectrum subtraction;

wherein the step of predicting the blood constituents concentration further comprises:

preparing a multi-regression analyzing mode;

calibrating the multi-regression analyzing model by supplying plural sample data comprising spectrum subtractions obtained non-invasively from a living body having known blood constituent concentrations as explanatory variables and the known blood constituent concentrations as objective variables, using the non-invasive blood constituents measuring instrument;

inputting the output data of the spectrum subtraction generator obtained from the living body whose blood constituents are unknown to the blood constituent concentrations predictor; and outputting the blood constituent concentrations calculated by the calibrated multi-regression analyzing model in the blood constituent concentrations predictor.

10. A method for non-invasively measuring blood constituents claimed in claim 9, wherein the multi-regression analyzing model is constructed using the PLS or PCR method.

11. A method for non-invasively measuring blood constituents claimed in claim 9, wherein the light includes plural wavelengths in the wavelength band of 800-2400 nm arranged at an interval of 3 nm.

12. A method for non-invasively measuring blood glucose concentration comprising the steps of: irradiating a light in the near infrared range containing plural wavelengths to a living body whose blood glucose concentration is unknown; detecting light transmitted through or reflected from the living body and converting it into an electric signal; separating the light into plural wavelengths in the near infrared range at an interval of 40-50 ms period of time; analyzing spectrum of the light transmitted through the living body or reflected therefrom at different times having a shorter time intervals than a cycle time of the arterial waveform cycle using the converted electric signal; generating a plurality of spectrum subtractions from the spectrum of the light measured by the spectrum analyzer at any two different times corresponding to time intervals of 40-50 ms; and predicting corresponding blood glucose concentration from the spectrum subtraction;

wherein the step of predicting the blood glucose concentration further comprises:

preparing a multi-regression analyzing model;

calibrating the multi-regression analyzing model by supplying plural sample data comprising spectrum subtractions obtained non-invasively from a living body having known blood glucose concentrations as explanatory variables and the known blood glucose concentrations as objective variable using a non-invasive blood glucose measuring instrument;

inputting the output data of the spectrum subtraction generator obtained from the living body whose blood glucose concentrations are is unknown to the blood glucose concentrations predictor; and outputting the blood glucose concentrations calculated by the calibrated multi-regression analyzing model in the blood glucose concentrations predictor.

13. A method for non-invasively measuring blood glucose concentrations claimed in claim 12, wherein the multi-regression analyzing model is constructed using the PLS or PCR method.

14. A method for non-invasively measuring blood glucose concentrations claimed in claim 12, wherein the light includes plural wavelengths in the wavelength band of 800-2400 nm arranged at an interval of 3 nm.

* * * * *

UNITED STATES PATENT AND TRADEMARK OFFICE
CERTIFICATE OF CORRECTION

PATENT NO. : 8,275,433 B2
APPLICATION NO. : 11/819324
DATED : September 25, 2012
INVENTOR(S) : Ken-ichi Yamakoshi It is certified that error appears in the above-identified patent and that said Letters Patent is hereby corrected as shown below:

In the Claims:

Column 15, Claim 12, Line 7:
Please delete "objective variable" and replace with --objectives variables--

Column 15, Claim 12, Line 11:
Please delete "are is unknown" and replace with --are unknown--

Signed and Sealed this
Seventeenth Day of September, 2013

Teresa Stanek Rea
*Deputy Director of the United States Patent and Trademark Office*